United States Patent
Palmieri

(10) Patent No.: US 7,485,214 B2
(45) Date of Patent: Feb. 3, 2009

(54) MICROFLUIDIC DEVICE AND METHOD OF LOCALLY CONCENTRATING ELECTRICALLY CHARGED SUBSTANCES IN A MICROFLUIDIC DEVICE

(75) Inventor: Michele Palmieri, Agrate Brianza (IT)

(73) Assignee: STMicroelectronics S. r. l., Agrate Brianza (IT)

( * ) Notice: Subject to any disclaimer, the term of this patent is extended or adjusted under 35 U.S.C. 154(b) by 593 days.

(21) Appl. No.: 11/015,633

(22) Filed: Dec. 17, 2004

(65) Prior Publication Data

US 2005/0155860 A1  Jul. 21, 2005

(30) Foreign Application Priority Data

Dec. 23, 2003 (EP) .................................. 03425822

(51) Int. Cl.
*B03C 5/02* (2006.01)
(52) U.S. Cl. ................ 204/660; 204/600; 204/601; 204/660
(58) Field of Classification Search ................ 137/828; 438/49, 50, 51, 52, 22; 435/283.1, 287.2; 257/536, 382, 14; 204/454, 451, 601, 600
See application file for complete search history.

(56) References Cited

U.S. PATENT DOCUMENTS

| | | | |
|---|---|---|---|
| 4,993,143 A | 2/1991 | Sidner et al. | |
| 5,133,844 A | 7/1992 | Stevens | |
| 5,429,734 A | 7/1995 | Gajar et al. | |
| 5,582,701 A | 12/1996 | Geis et al. | |
| 5,637,469 A | 6/1997 | Wilding et al. | |
| 5,639,423 A | 6/1997 | Northrup et al. | |
| 5,922,591 A | 7/1999 | Anderson et al. | |
| 5,939,312 A | 8/1999 | Baier et al. | |
| 5,942,443 A | 8/1999 | Parce et al. | |
| 6,046,056 A | 4/2000 | Parce et al. | |
| 6,136,171 A | 10/2000 | Frazier et al. | |
| 6,136,630 A * | 10/2000 | Weigold et al. | ................ 438/50 |
| 6,261,431 B1 | 7/2001 | Mathies et al. | |
| 6,267,858 B1 | 7/2001 | Parce et al. | |
| 6,376,291 B1 | 4/2002 | Barlocchi | |
| 6,518,022 B1 | 2/2003 | Sosnowski et al. | |
| 6,537,437 B1 | 3/2003 | Galambos | |

(Continued)

FOREIGN PATENT DOCUMENTS

JP          60251873         * 12/1985

(Continued)

OTHER PUBLICATIONS

Canter, On-Chip Amplification of Genomic DNA with Short Tandem Repeat and Single Nucleotide Polymorphism Analysis, Nanogen website.

(Continued)

*Primary Examiner*—Nam X Nguyen
*Assistant Examiner*—Bach T Dinh
(74) *Attorney, Agent, or Firm*—Baker & McKenzie LLP

(57) ABSTRACT

A microfluidic device includes a microfluidic circuit, having an axis, and an electric field generator, arranged to establish an electric field (E) within at least a section of the microfluidic circuit, the electric field (E) being oriented transversally to the axis. The electric field is used to locally concentrate charged molecules, thus increasing the reaction rate.

11 Claims, 3 Drawing Sheets

U.S. PATENT DOCUMENTS

| | | |
|---|---|---|
| 6,670,257 B1 | 12/2003 | Barlocchi |
| 6,673,593 B2 | 1/2004 | Mastromatteo et al. |
| 6,710,311 B2 | 3/2004 | Villa et al. |
| 6,727,479 B2 | 4/2004 | Villa |
| 6,770,471 B2 | 8/2004 | Barlocchi et al. |
| 2001/0036672 A1 | 11/2001 | Anderson et al. |
| 2002/0022261 A1 | 2/2002 | Anderson et al. |
| 2002/0055167 A1 | 5/2002 | Pourahmadi et al. |
| 2002/0060156 A1 | 5/2002 | Mathies et al. |
| 2002/0066319 A1 | 6/2002 | Beach et al. |
| 2002/0068334 A1 | 6/2002 | Carrino et al. |
| 2002/0068357 A1 | 6/2002 | Mathies et al. |
| 2002/0071785 A1 | 6/2002 | Beach et al. |
| 2002/0084510 A1* | 7/2002 | Jun et al. .................... 257/536 |
| 2002/0097900 A1 | 7/2002 | Arena et al. |
| 2002/0117659 A1* | 8/2002 | Lieber et al. ................. 257/14 |
| 2003/0070677 A1 | 4/2003 | Handique et al. |
| 2003/0127329 A1* | 7/2003 | DeVoe et al. ................ 204/454 |
| 2004/0096964 A1 | 5/2004 | Mastromatteo |
| 2004/0227207 A1 | 11/2004 | Barlocchi |
| 2005/0247357 A1* | 11/2005 | Welle ........................ 137/828 |

FOREIGN PATENT DOCUMENTS

| | | |
|---|---|---|
| WO | WO 96/15576 | 5/1996 |
| WO | WO 98/25701 | 6/1998 |

OTHER PUBLICATIONS

Zhang, N., Automated and Integrated System for Thigh-Throughput DNA Genotyping Directly from Blood, Analytical Chemistry, Mar. 15, 1999, pp. 1138-1145, vol. 71(6).

Search report, EP 03 425 822 filed May 26, 2004.

* cited by examiner

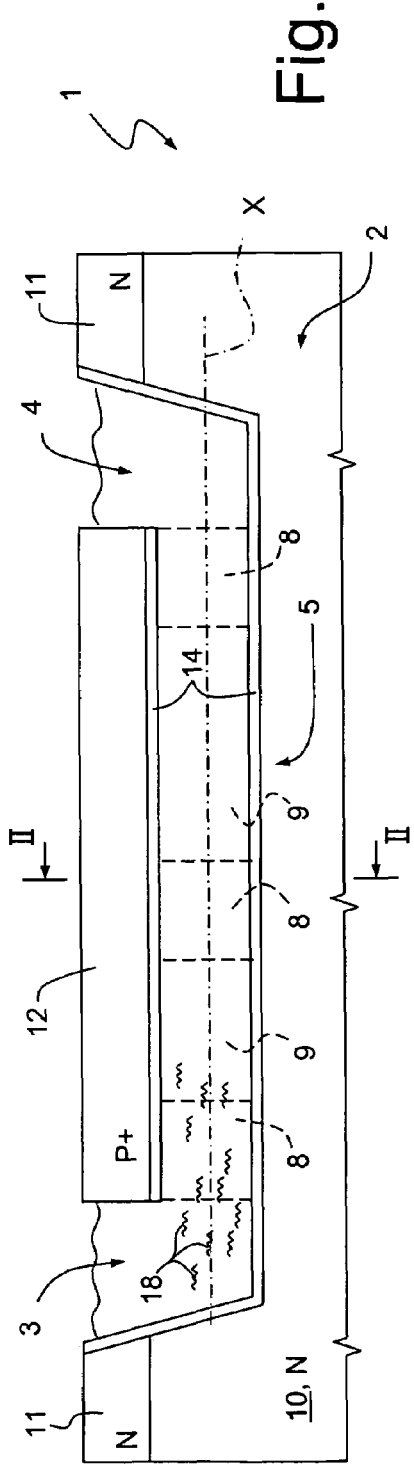
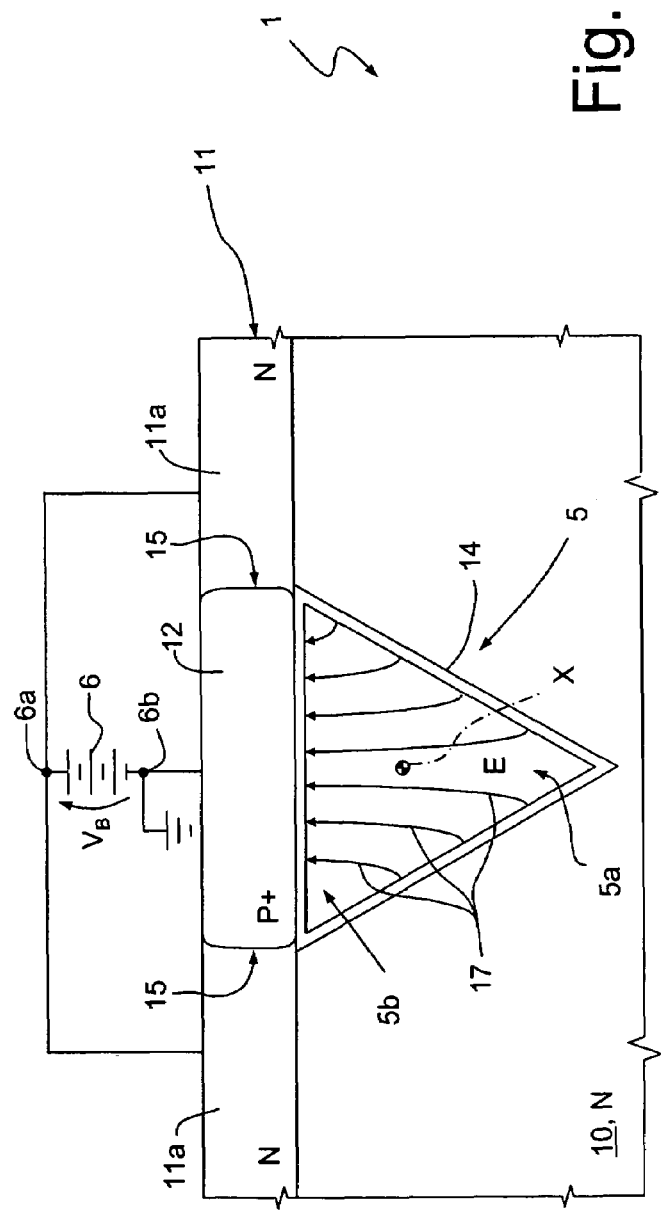
Fig. 1
Fig. 2

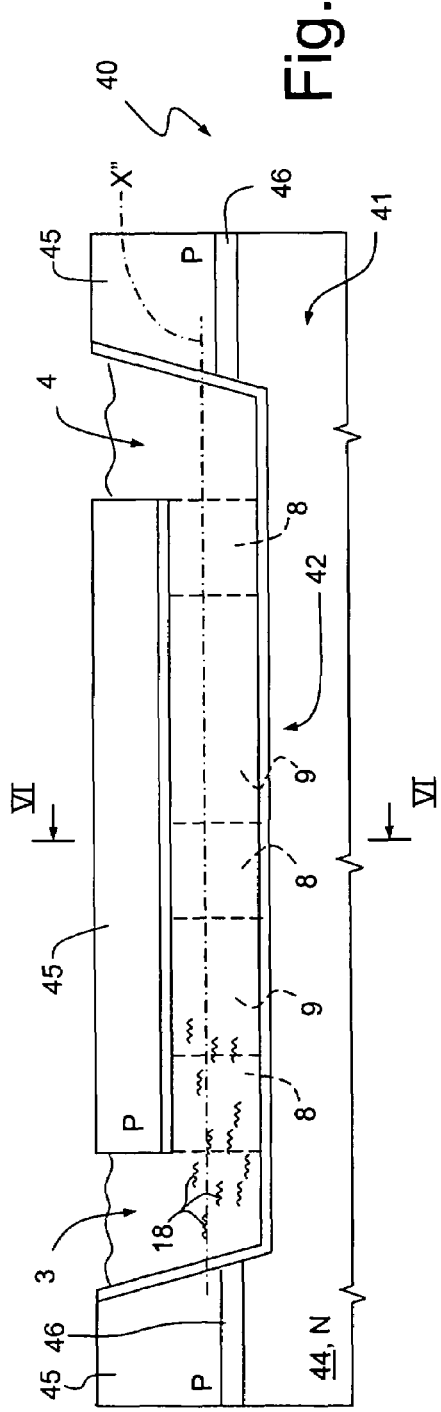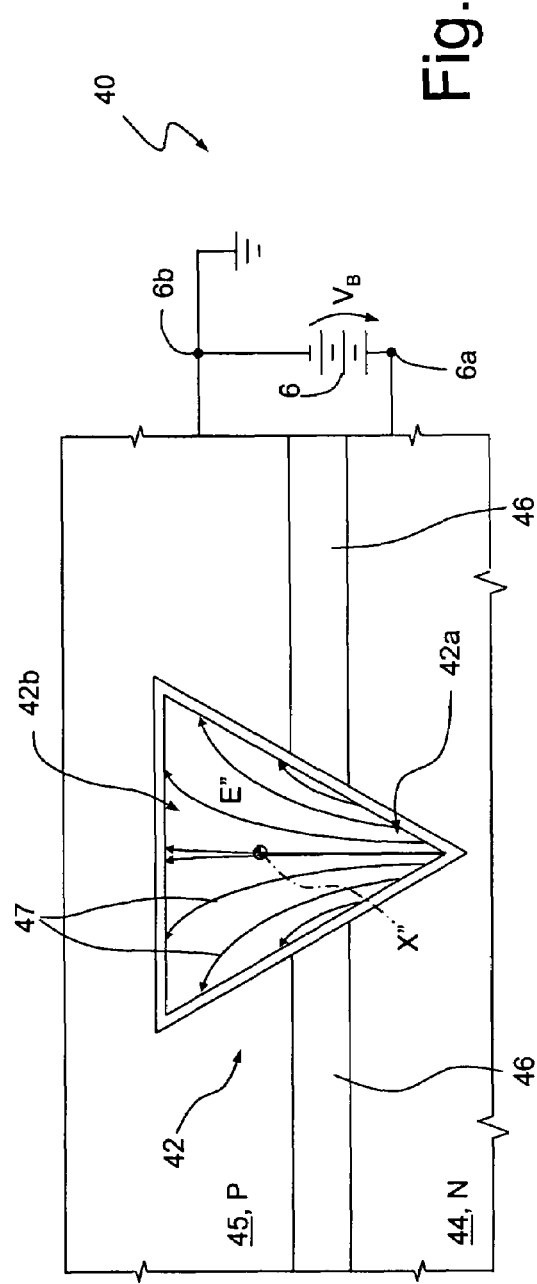

MICROFLUIDIC DEVICE AND METHOD OF LOCALLY CONCENTRATING ELECTRICALLY CHARGED SUBSTANCES IN A MICROFLUIDIC DEVICE

PRIOR RELATED APPLICATIONS

This application claims priority to application EP03425822.8, filed on Dec. 23, 2003.

FEDERALLY SPONSORED RESEARCH

Not applicable.

SEQUENCE LISTING

Not applicable.

FIELD OF THE INVENTION

The present invention relates to a microfluidic device, in particular a chemical microreactor for the analysis of charged molecules, such as nucleic acid, and to a method for increasing the local concentration of charged molecules in the device.

BACKGROUND OF THE INVENTION

As is known, microfluidic devices may be exploited in a number of applications, and are particularly suited to be used as chemical microreactors. Thanks to the design flexibility allowed by semiconductor micromachining techniques, single integrated devices have been made that are capable of carrying out individual processing steps or even an entire chemical process.

In general, microfluidic chemical microreactors are provided with a microfluidic circuit, comprising a plurality of processing chambers in mutual fluidic connection through microchannels. In the most advanced microfluidic devices the microchannels are buried in a substrate and/or in an epitaxial layer of a semiconductor chip.

Substances to be processed, which are dispersed in a fluid medium, are supplied to one or more inlet reservoirs of the microfluidic circuit and are moved therethrough. Chemical reactions take place along the microfluidic circuit, either in the processing chambers or in the microchannels.

For example, microfluidic devices are widely employed in biochemical processes, such as nucleic acid analysis. Such microreactors may also be called "Labs-On-Chip." In general, the microfluidic device may comprise one or more mixing chambers, heating chambers, dielectrophoretic cells, micropumps, amplification chambers, detection chambers, capillary electrophoresis channels, and the like. Heaters, sensors, controls, and the like may also be incorporated into the device.

Some reactions, however, are lengthy and their efficiency and speed depend on several factors, such as the likelihood of interaction between the substances involved. In particular, the likelihood of interaction is greatly affected by the concentration of the reagents.

For example, DNA amplification involves a series of enzyme-mediated reactions whose final result are identical copies of the target nucleic acid. In particular, Polymerase Chain Reaction (PCR) is a cyclical process where the number of DNA molecules substantially doubles at every iteration, starting from a mixture comprising target DNA, enzymes (typically a DNA polymerase such as TAQ), primers, the four dNTPs, cofactor, and buffer.

During a cycle, double stranded DNA is first separated into single strands (denatured). Then the primers hybridize to their complementary sequences on either side of the target sequence. Finally, DNA polymerase extends each primer, by adding nucleotides that are complementary to the target strand. This doubles the DNA content and the cycle is repeated until sufficient DNA has been synthesized.

Although PCR allows the production of millions of copies of target sequences in few hours, in many cases its efficiency and speed might be improved by increasing the concentration of the reagents. Similarly, end-point detection of amplified DNA (amplicons) by hybridization is highly concentration dependent.

However, in known microfluidic devices the reagents are merely supplied and moved through the microfluidic circuit (e.g. by a micropump coupled thereto). Thus, the reagents tend to be uniformly distributed and the concentration is exclusively determined by their amount and by the geometry of the microfluidic circuit.

The aim of the present invention is to provide a microfluidic device and a method for increasing the concentration of electrically charged substances in a microfluidic device, which overcome the above-described problem and, in particular, improve reaction efficiency by locally increasing reagent concentration.

SUMMARY OF THE INVENTION

According to the present invention there are provided a microfluidic device and a method for increasing the concentration of electrically charged substances in a microfluidic device, as defined in claims 1 and 11, respectively.

In particular, the microfluidic device includes a microfluidic circuit having an axis, and an electric field generator, arranged to establish an electric field (E) within at least a section of the microfluidic circuit, the electric field (E) being oriented transversally to the axis. The electric field is used to locally concentrate charged molecules, thus increasing the reaction rate. The electric field is established using N-type and P-type semiconductor materials and is thus very simple and cost effective to manufacture.

In a preferred embodiment, the microfluidic circuit comprises a buried channel, as defined and described in U.S. Pat. Nos. 6,770,471, 6,673,593, US20040096964, US20040227207, U.S. Pat. Nos. 6,710,311, 6,670,257, 6,376,291 and their related patents and applications (each incorporated by reference in their entirety).

In a preferred embodiment, the method can be applied to an integrated microreactor, but it is equally applicable to partially integrated microdevices. Further, although we have exemplified the inventive concept by reference to locally concentrating nucleic acid, it can be applied to any other charged molecules, such as proteins, glycoproteins, phospholipids, and the like.

For a better understanding of the present invention, some preferred embodiments are described, purely by way of non-limiting example, with reference to the attached drawings.

BRIEF DESCRIPTION OF THE DRAWINGS

FIG. 1 is a lateral view of an integrated microfluidic device according to a first embodiment of the present invention, sectioned along a longitudinal plane.

FIG. 2 is an enlarged cross section across the integrated microfluidic device of FIG. 1, taken along line II-II of FIG. 1.

FIG. 5 is a lateral view of an integrated microfluidic device according to a third embodiment of the present invention, sectioned along a longitudinal plane.

FIG. 6 is an enlarged cross section across the integrated microfluidic device of FIG. 5, taken along line VI-VI of FIG. 5.

DESCRIPTION OF EMBODIMENTS OF THE INVENTION

Figure 3:
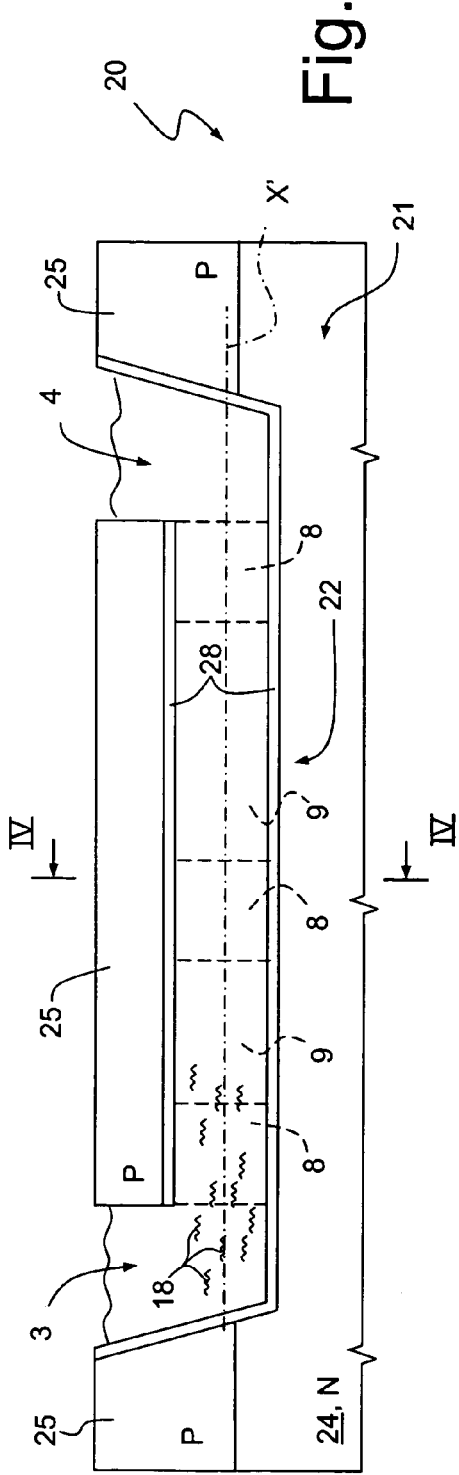
FIG. 3 is a lateral view of an integrated microfluidic device according to a second embodiment of the present invention, sectioned along a longitudinal plane.

With reference to FIGS. 1 and 2, a semiconductor chip 1 houses a microfluidic device 2, in particular a chemical microreactor for nucleic acid analysis in the embodiment hereinafter described. The microfluidic device 2 comprises inlet and outlet reservoirs 3, 4, both open at an upper surface of the chip 1, and a microfluidic circuit 5, which is fluidly coupled to the inlet reservoir 3 and the outlet reservoir 4. Moreover, the microfluidic device 2 is provided with a voltage source 6, that is only schematically illustrated in FIG. 2. A micropump, of a known type and not shown in the drawings for the sake of simplicity, is coupled to the microfluidic circuit 5 and provides for moving a fluid medium containing substances to be processed through the microfluidic circuit 5.

Processing chambers 8 are formed at respective sections of the microfluidic circuit 5 and are mutually connected through connection segments 9. The processing chambers 8 are per se known and are not illustrated in detail. For example, the microfluidic circuit 5 may comprise mixing chambers, dielectrophoretic cells, an amplification or other reaction chamber, and a detection chamber.

In the embodiment described, the microfluidic circuit 5 extends along a substantially rectilinear path and has a longitudinal axis X, which is rectilinear and corresponds to the direction of movement of the fluid medium. However, it is understood that the microfluidic circuit 5 may have a plurality of non-aligned sections as well (rectilinear sections forming right angles or bent sections, for example). In this case, each section extends along a respective rectilinear or curvilinear axis, which corresponds to direction of movement of the fluid medium.

The microfluidic circuit 5 is buried inside the chip 1. In greater detail, the chip 1 comprises a substrate 10, of monocrystalline silicon, and a structural layer 11 of semiconductor material, for example an epitaxial or a polycrystalline layer. Both the substrate 10 and the structural layer 11 have N-type conductivity. Moreover, a conductive region 12, of P-type, extends through the structural layer 11, above the microfluidic circuit 5. The microfluidic circuit 5, which is preferably formed as a microfluidic channel having triangular cross-section (FIG. 2), extends within the substrate 10 and is upwardly delimited by the conductive region 12.

Preferably, side walls 5a and an upper wall 5b of the microfluidic circuit 5 are coated with a silicon dioxide layer 14, having a thickness e.g. of between 0.1 µm and 1 µm. However, other coatings suitable for the application of interest may be used.

In practice, the processing chambers 8 and the connection segments 9 of the microfluidic circuit 5 are surrounded partly by an N-type region, comprising the substrate 10 and an external portion 11a of the structural layer 11 around the conductive region 12, and partly by a P-type region, i.e. the conductive region 12 itself. N-type region 10, 11a and P-type region 12 preferably extend along the whole processing chambers 8. Furthermore, P-N junctions 15 are formed between the conductive region 12 and the above defined N-type region, in particular the external portion 11a of the structural layer 11. It is understood that conductive region 12 may overlap the substrate 10; in this case, the P-N junctions 15 extend to the substrate 10.

The voltage source 6 has a positive terminal 6a connected to the external portion 11a of the structural layer 11, and a negative terminal 6b connected to the conductive region 12 (here grounded), and supplies a bias voltage VB, e.g. of 5 V. Hence, when the voltage source 6 is activated, the P-N junctions 15 are reverse biased and a voltage drop equal to the bias voltage VB is established between the external portion 11a of the structural layer 11 and the conductive region 12. Accordingly, the same voltage drop is established between the side walls 5a (surrounded by the substrate 10, of N-type) and the upper wall 5b (overlaid by the conductive region 12, of P-type) of the microfluidic circuit 5, thus establishing an electric field E.

In FIG. 2, the electric field E is illustrated through field lines 17, starting from the side walls 5a (set at the bias voltage VB) and arriving at the upper wall 5b (grounded). More specifically, the electric field E is substantially transverse to the longitudinal axis X of the microfluidic circuit 5 (see also FIG. 1). The silicon dioxide layer 14 is very thin and does not significantly affect the distribution of the field lines 17 within the microfluidic circuit 5.

In order to carry out a nucleic acid analysis through the microfluidic device 2, substances to be processed (e.g. DNA or RNA molecules, polymerase, primers, and dNTPs or NTPs) are provided in the inlet reservoir 3 and moved toward the outlet reservoir 4 by the micropump (not shown).

As is well known, DNA 18 is negatively charged because it has an alternating phosphate-sugar backbone, each phosphate carrying a negative charge. Hence, DNA 18 (illustrated here as single stranded DNA) is subject to the action of the electric field E, once the voltage source 6 has been activated. In particular, the DNA 18 migrates toward high voltage regions according to its negative charge and to the field lines 17. In other words, the DNA 18 tends to concentrate in the vicinity of the side walls 5a, which are at the bias voltage VB, whereas the microfluidic circuit 5 is depleted of DNA 18 around the upper wall 5b, which is maintained at a lower voltage (ground). Therefore, the concentration of DNA 18 is increased around the positive-biased regions of the microfluidic circuit 5 with respect to a homogeneous concentration over a cross-section of the microfluidic circuit 5.

It is clear from the above description that the invention advantageously allows the user to locally modify the concentration of DNA or other electrically charged reagents, in order to favor interactions and improve the speed and the efficiency of the reactions. Moreover, the integration of the microfluidic device 2 inside the chip 1 is cheap and simple, since only standard microfabrication steps are required.

Figure 4:
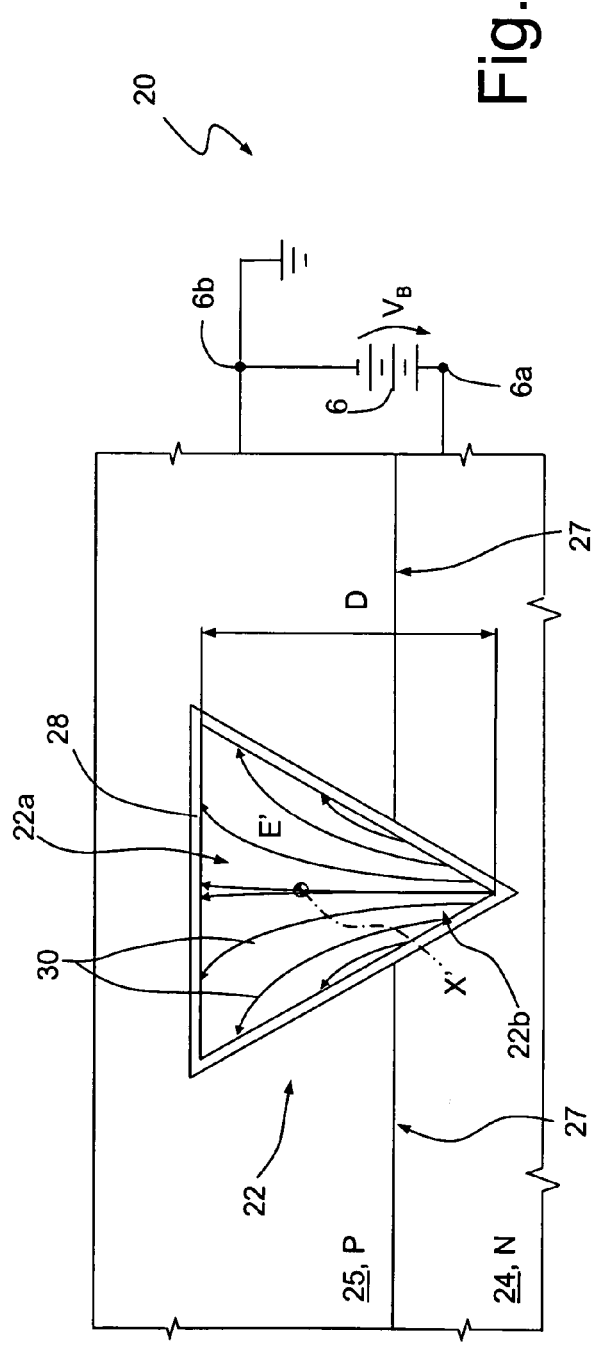
FIG. 4 is an enlarged cross section across the integrated microfluidic device of FIG. 3, taken along line IV-IV of FIG. 3.

According to a second embodiment shown in FIG. 3 and 4, where parts already illustrated are indicated with the same reference numbers, a microfluidic device 21 is integrated in a semiconductor chip 20, and comprises the inlet and outlet reservoirs 3, 4, the voltage source 6 and a microfluidic circuit 22, similar to the microfluidic circuit 5 of FIGS. 1, 2. In particular, the microfluidic circuit 22 has a triangular cross section and a longitudinal axis X', and is buried within the semiconductor chip 20. More precisely, a lower portion 22b of the microfluidic circuit 22, corresponding to approximately one third of its depth D, extends within a substrate 24 of the semiconductor chip 20, of N-type. An upper portion 22a of the microfluidic circuit 22 is both laterally and upwardly surrounded by a structural layer 25, of P-type. Moreover, the substrate 24 and the structural layer 25 are contiguous to each other and form P-N junctions 27. Also in this case, the walls of the microfluidic circuit 22 are coated with a thin silicon dioxide layer 28.

The positive terminal 6a and the negative terminal 6b of the voltage source 6 are connected to the substrate 24 and to the structural layer 25 (here grounded), respectively. Hence, when the voltage source 6 is activated, the P-N junctions 27 are reverse-biased (with the bias voltage VB). Furthermore, a voltage field E' is established within the microfluidic circuit 22, owing to the voltage drop between the substrate 24 and the structural layer 25. In FIG. 4, the electric field E' is illustrated through field lines 30 originating in the lower portion 22b and arriving at the upper portion 22a of the microfluidic circuit 22.

Hence, when the voltage source 6 is activated, the DNA 18 or other negatively charged substances tend to concentrate at the lower portion 22b, which is surrounded by the N-type substrate 24 of the chip 20.

Further advantages are provided by the above-described embodiment. In the first place, higher concentration of DNA 18 or other negatively charged substances may be obtained because the negatively charged particles are confined in a small volume by the electric field E'. Second, the microfluidic device 21 is even simpler to manufacture, because the microfluidic circuit 21 is mostly embedded in the structural layer 25, rather than in the substrate 24.

A third embodiment of the invention is shown in FIG. 5 and 6, where parts already illustrated are designated with the same reference numbers. In this case, a microfluidic device 41 is integrated in a semiconductor chip 40, and comprises the inlet and outlet reservoirs 3, 4, the voltage source 6 and a microfluidic circuit 42, similar to the microfluidic circuit 5 of FIGS. 1, 2. In particular, the microfluidic circuit 42 has a triangular cross section and a longitudinal axis X", and is buried within the semiconductor chip 40. More precisely, a lower portion 42a of the microfluidic circuit 42 extends within a substrate 44 of the semiconductor chip 40, which is of N-type and is connected to the positive terminal 6a of the voltage source 6. An upper portion 42b of the microfluidic circuit 42 is both laterally and upwardly surrounded by a structural layer 45, which is of P-type and is connected to the negative terminal 6b of the voltage source 6. Moreover, the substrate 44 and the structural layer 45 are separated from each other by an insulating layer 46, here of deposited silicon dioxide and having a thickness of between 1 μm and 50 μm.

Hence, a high bias voltage VB, even of several tens of volts, may be advantageously applied between the substrate 44 and the structural layer 45, without danger of inverse breakdown. Accordingly, also a high electric field E'" (lines 47 in FIG. 6) may be established within the microfluidic circuit 42 and high concentration of reagents can be achieved. Moreover, the substrate 44 and the structural layer 45 may also have the same type of conductivity, since the insulating layer 46 prevents any current flow therebetween.

Finally, it is clear that numerous modifications and variations may be made to the microfluidic device and to the methods described and illustrated herein, all falling within the scope of the invention, as defined in the attached claims. For example, the semiconductive regions (substrate, structural layer, conductive region) of the chip housing the microfluidic device may have dual conductivity with respect to those described above. Accordingly, either the concentration of positively charged substances in the lower portion or the concentration of negatively charged substances in the upper portion of the microfluidic circuit is increased. The microfluidic circuit may also have a different configuration, e.g. its cross section may have rectangular or circular shape.

The invention claimed is:

1. A microfluidic device, comprising:
   a) a microfluidic circuit having longitudinal axis; and
   b) an electric field generating means arranged to establish an electric field transverse to said longitudinal axis within at least a section of said microfluidic circuit;
   wherein said electric field generating means comprises:
   i) a first semiconductor region having a first type of conductivity and a second semiconductor region having an opposite type of conductivity; and
   ii) a voltage source for supplying a bias voltage between said first and said second semiconductor regions in order to concentrate an electrically charged substance in a portion of the microfluidic circuit; and
   iii) wherein at least said section of said microfluidic circuit is between said first semiconductor region and said second semiconductor region, and wherein said first and second semiconductor regions being arranged to form at least one P-N junction.

2. The microfluidic device of claim 1, wherein said microfluidic circuit extends within said first semiconductor region and is upwardly delimited by said second semiconductor region.

3. The microfluidic device of claim 1, wherein said first semiconductor region comprises a substrate.

4. The microfluidic device of claim 3, wherein said second semiconductor region comprises at least a portion of a structural layer.

5. The microfluidic device of claim 1, wherein said first and said second semiconductor regions extend along the whole length of said section of said microfluidic circuit.

6. The microfluidic device of claim 1, wherein said voltage source is a negative voltage source.

7. The microfluidic device of claim 1, wherein said microfluidic circuit is formed as a microfluidic channel.

8. The microfluidic device of claim 7, wherein said channel is a buried channel.

9. A method for increasing the concentration of electrically charged substances in a microfluidic device, comprising the steps of:
   a) applying an electrically charged substance to a microfluidic circuit of a microfluidic device, said microfluidic circuit having longitudinal axis and being between a first semiconductor region having a first type of conductivity and a second semiconductor region having an opposite type of conductivity;
   b) providing a bias voltage between said first and second semiconductor regions;
   c) thereby establishing an electric field within at least a section of said microfluidic circuit, said electric field being oriented transversally to said longitudinal axis, and thereby concentrating said electrically charged substance;
   wherein said first and second semiconductor regions are arranged to form at least one P-N junction and providing a bias voltage comprises reverse biasing said P-N junction.

10. The method of claim 9, wherein the electrically charged substance is nucleic acid.

11. The method of claim 9, wherein the electrically charged substance is DNA.

* * * * *